United States Patent

Hashizume et al.

Patent Number: 5,164,512
Date of Patent: Nov. 17, 1992

[54] OXIDIZABLE COLOR PRODUCING REAGENT

[75] Inventors: Kazunari Hashizume, Wakayama; Haruhiko Sugiyama, Shiga, both of Japan

[73] Assignee: Wako Pure Chemical Industries, Ltd., Osaka, Japan

[21] Appl. No.: 540,252

[22] Filed: Jun. 19, 1990

[30] Foreign Application Priority Data

Jun. 21, 1989 [JP] Japan ............................ 1-158905
Jun. 22, 1989 [JP] Japan ............................ 1-160367

[51] Int. Cl.$^5$ ............................ C07D 233/64
[52] U.S. Cl. ............................ 548/334.1
[58] Field of Search ............................ 548/341

[56] References Cited

PUBLICATIONS

Patent Abstracts of Japan, vol. 10, No. 383 (C-393)[2440], Dec. 1986.
Patent Abstracts of Japan, vol. 11, No. 75 (C-408)[2522], Mar. 1987.
Patent Abstracts of Japan, vol. 11, No. 69 (C-407)[2516], Mar. 1987.

Primary Examiner—Floyd D. Higel
Assistant Examiner—Lenora Miltenberger
Attorney, Agent, or Firm—Armstrong & Kubovcik

[57] ABSTRACT

A triarylimidazole derivative of the formula:

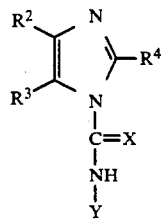

wherein X is O or S; Y is an arylsulfonyl group, an alkyl group, etc.; $R^2$, $R^3$ and $R^4$ are independently an aryl group, etc., is stable in water or a buffer solution, high in measuring sensitivity and is suitable as an oxidizable color producing reagent for determining hydrogen peroxide, etc. generated by enzymatic reaction in a living body sample.

6 Claims, 2 Drawing Sheets

OXIDIZABLE COLOR PRODUCING REAGENT

BACKGROUND OF THE INVENTION

This invention relates to a triarylimidazole derivative as an oxidizable color producing reagent, and a process for quantitatively determining an oxidizing substance or a peroxidase-like substance using said oxidizable color producing reagent.

Measurement of components in living body samples such as blood, urine, and the like has been essential for diagnosis of diseases, elucidation of diseases and judgement of the course of remedy, since changes of measured values greatly relate to diseases. Thus, there have been developed processes for measuring various kinds of trace amount components such as cholesterol, triglyceride, glucose, uric acid, phospholipids, bile acid, monoamine oxidase, etc. in blood. It is well known that these processes are very useful for diagnosis of diseases.

At present, as processes for measuring serum components, it is widely used in general so-called "enzymatic method" wherein an enzymatic reaction is carried out by either using an enzyme specifically act on an objective component when the objective component is other than enzyme, or using a compound as a substrate when the objective component is an enzyme, and measuring the product of the enzymatic reaction to obtain the amount of the objective component. Among these processes, there is increasingly used a process for measuring the amount of objective component comprising producing $H_2O_2$ corresponding to the objective component by acting a hydrogen peroxide generating enzyme such as oxidase, leading the hydrogen peroxide to a color producing system using peroxidase and an oxidizable color producing reagent which is a color producing component, and measuring the color produced colorimetrically, with the development of oxidizable color producing reagents. For example, $H_2O_2$ produced by a combination of cholesterol-cholesterol oxidase, triglyceridelipoprotein lipase-glycerol oxidase, uric acid-uricase, or the like is led to a color forming system by using peroxidase (POD) and an oxidizable color producing reagent, and absorbance of the color produced is measured to determine the amount of objective component. Typical examples of the oxidizable color reagent are a combination of 4-aminoantipyrine and a phenolic compound or an N,N-disubstituted aniline compound, a combination of 3-methyl-2-benzothiazolinonehydrazone (MBTH) and an aniline compound, 2,2'-azinobis-(3-ethylbenzothiazoline-6-sulfonic acid), triphenylmethane series leuco dyes, diphenylamine derivatives, benzidine derivatives, o-toluidine derivatives, o-phenylenediamines, etc.

But, almost all of these oxidizable color producing reagents except for the diphenylamine derivatives have color producing wavelengths of 600 nm or less and are easily influenced by serum components such as bilirubin, hemoglobin, etc. (easily influenced by coloring matters in urine in the case of measuring urine components). Further, there is another problem in that any chromogens except for the combined reagents with 4-aminoantipyrine and a part of triphenylmethane leuco dyes are low in stability.

On the other hand, as chromogens relatively good in stability and having a color producing wavelength at a relatively longer wavelength side, there have been disclosed triarylimidazole derivatives which are dye precursors (leuco dyes) (e.g. Japanese Patent Examined Publication Nos. 57-5519 and 57-26118, Japanese Patent Unexamined Publication Nos. 58-4557, 61-174267 and 61-227,570, U.S. Pat. No. 3,297,710, etc.). But even if these triarylimidazole derivatives are used as color producing component in the measurement of trace amount components in living body samples such as serum, urine, etc., no satisfactory results are obtained.

SUMMARY OF THE INVENTION

It is an object of the present invention to provide a triarylimidazole derivative showing almost no lowering in color producing sensitivity by serum components, high measuring sensitivity and having an absorption maximum at a longer wavelength side. It is another object of the present invention to provide a process for measuring the amount of an oxidizing substance or a substance which has peroxidase activity with high precision using said derivative as a color producing component.

The present invention provides a triarylimidazole derivative represented by the formula:

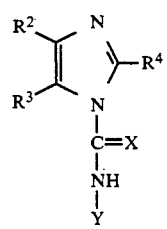

(I)

wherein X is an oxygen atom or a sulfur atom; Y is, in the case of X=O, an arylsulfonyl group which may have one or more substituents, an alkylsulfonyl group which may have one or more substituents, a carboxyl group or an alkoxycarbonyl group (hereinafter defined as $Y=R^1$), or in the case of X=S, a hydrogen atom, an alkyl group which may have one or more substituents, an aryl group which may have one or more substituents, or a hydroxyl group (hereinafter defined as $Y=R^5$); $R^2$, $R^3$ and $R^4$ are independently an aryl group which may have one or more substituents, provided that at least one of $R^2$, $R^3$ and $R^4$ is a substituted phenyl group having a hydroxyl group or an amino group which may have one or more substituents, at the para-position with regard to the imidazole ring.

The present invention also provide a process for measuring the amount of an oxidizing substance using the triarylimidazole derivative of the formula (I) as a color producing component.

The present invention further provide a process for measuring the amount of a substance which has peroxidase activity using the triarylimidazole derivative of the formula (I) as a color producing component.

DESCRIPTION OF THE PREFERRED EMBODIMENTS

Figure 1:
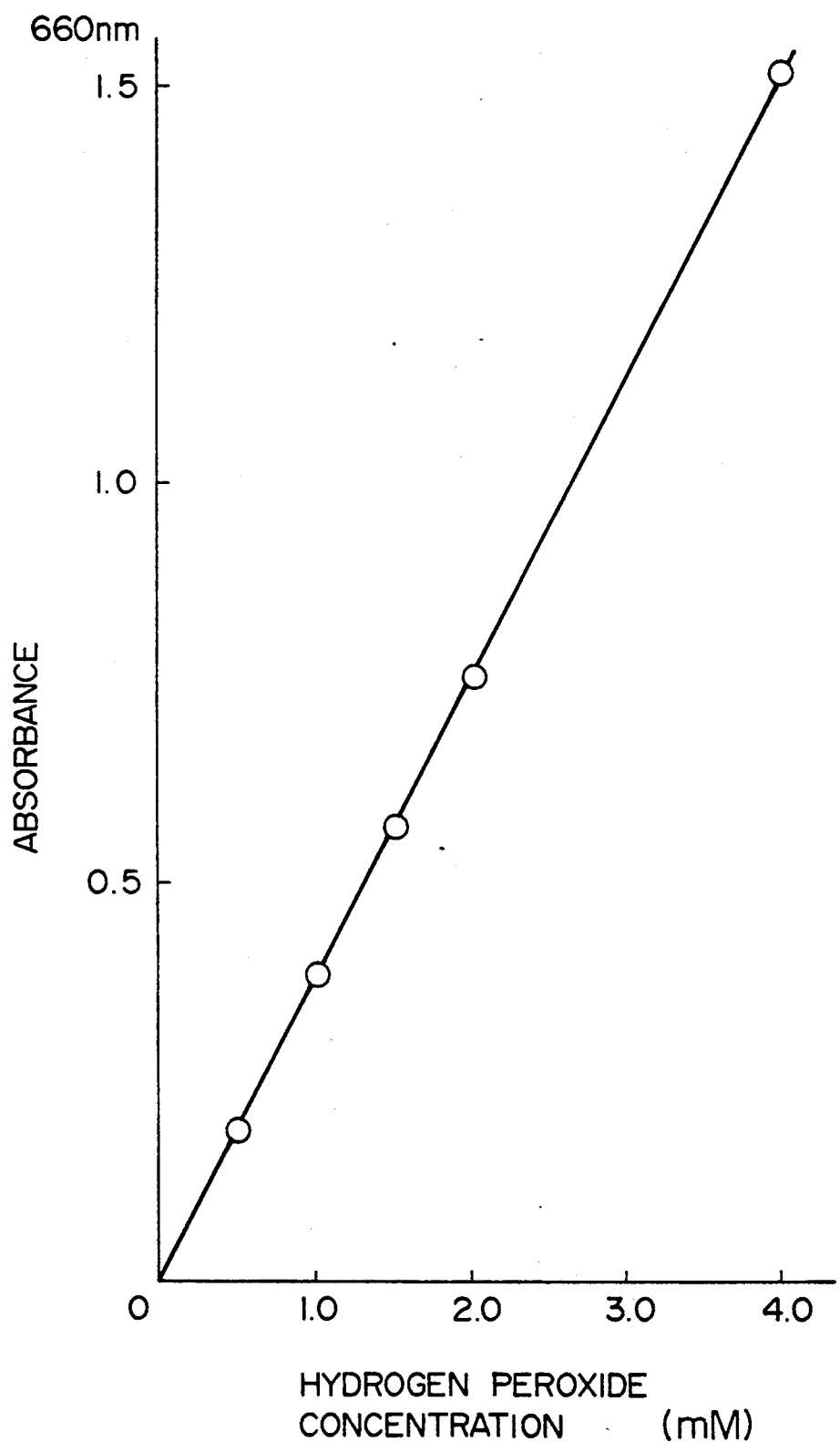
FIG. 1 is a calibration curve obtained in Example 6.

According to the present invention, since the special group of the formula:

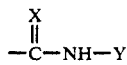

is attached to the imidazole ring, a phenomenon of inhibition of color production by substances co-present in living body samples such as serum, blood, urine, and the like can be suppressed at the least.

The triarylimidazole derivative of the present invention is represented by the formula:

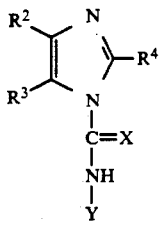

(I)

wherein X is an oxygen atom or a sulfur atom; Y is, in the case of X=O, an arylsulfonyl group which may have one or more substituents, an alkylsulfonyl group which may have one or more substituents, a carboxyl group or an alkoxycarbonyl group (hereinafter defined as $Y=R^1$), or in the case of X=S, a hydrogen atom, an alkyl group which may have one or more substituents, an aryl group which may have one or more substituents, or a hydroxyl group (hereinafter defined as $Y=R^5$); $R^2$, $R^3$ and $R^4$ are independently an aryl group which may have one or more substituents, provided that at least one of $R^2$, $R^3$ and $R^4$ is a substituted phenyl group having a hydroxyl group or an amino group which may have one or more substituents, at the para-position with regard to the imidazole ring.

In the formula (I), when X=O, Y can further be defined as $R^1$. Examples of the aryl moiety in the arylsulfonyl group which may have one or more substituents in the definition of $R^1$ are a phenyl group, a tolyl group, an ethylphenyl group, a naphthyl group, a methylnaphthyl group, etc. Examples of the substituents are a lower alkoxy group preferably having 1 to 4 carbon atoms such as methoxy, ethoxy, propoxy, etc.; a halogen atom such as iodine, bromine, chlorine, fluorine, etc.; an amino group, etc. Examples of the alkyl moiety in the alkylsulfonyl group which may have one or more substituents in the definition of $R^1$ are a lower alkyl group preferably having 1 to 4 carbon atoms (either straight-chain or branched-chain) such as methyl, ethyl, propyl, butyl, etc. Examples of the substituents are a lower alkoxy group preferably having 1 to 4 carbon atoms such as methoxy, ethoxy, propoxy, etc.; a hydroxyl group, a hydroxyethoxy group, etc. Examples of the alkoxy moiety in the alkoxycarbonyl group in the definition of $R^1$ are straight- or branched-chain lower alkoxy groups preferably having 1 to 4 carbon atoms such as methoxy, ethoxy, propoxy, etc. Further, $R^1$ can be a carboxyl group.

When X=S, Y can further be defined as $R^5$. Examples of the alkyl group in the definition of $R^5$ are straight- or branched-chain lower alkyl group preferably having 1 to 4 carbon atoms such as methyl, ethyl, propyl, butyl, etc. Examples of the substituents in the definition of the alkyl group which may have one or more substituents are a lower alkoxy group preferably having 1 to 4 carbon atoms such as methoxy, ethoxy, propoxy, etc.; a hydroxyl group, a hydroxyethoxy group, a carboxyl group, etc. Examples of the aryl moiety in the aryl group which may have one or more substituents in the definition of $R^5$ are a phenyl group, a tolyl group, an ethylphenyl group, a naphthyl group, a methylnaphthyl group, etc. Examples of the substituents are a lower alkoxy group preferably having 1 to 4 carbon atoms such as methoxy, ethoxy, propoxy, etc.; a halogen atom such as iodine, bromine, chlorine, fluorine, etc.; an amino group, a sulfo group, etc.

Examples of the aryl moiety in the aryl group which may have one or more substituents in the definition of $R^2$, $R^3$ and $R^4$ are a phenyl group, a tolyl group, an ethylphenyl group, a naphthyl group, a methylnaphthyl group, etc. Examples of the substituents are a lower alkoxy group which can be either straight-chain or branched preferably having 1 to 4 carbon atoms such as methoxy, ethoxy, propoxy, butoxy, etc.; an alkylcarbonyl group wherein the alkyl moiety thereof is a lower alkyl (either straight-chain or branched) group preferably having 1 to 4 carbon atoms such as methyl, ethyl, propyl, butyl, etc.; an arylcarbonyl group which may have one or more substituents wherein the aryl moiety thereof can be a phenyl group, a tolyl group, an ethylphenyl group, a naphthyl group, a methylnaphthyl group, etc., and the substituents thereof can be a straight- or branched-chain lower alkoxy group preferably having 1 to 4 carbon atoms such as methoxy, ethoxy, propoxy, butoxy, etc., a halogen atom such as iodine, bromine, chlorine or fluorine, or an amino group; an amino group which may have one or more substituents which can be a straight- or branched-chain lower alkyl group preferably having 1 to 4 carbon atoms such as methyl, ethyl, propyl or butyl, a hydroxyalkyl group such as hydroxymethyl, hydroxyethyl, hydroxypropyl, etc., a carboxyalkyl group such as carboxymethyl, carboxyethyl, carboxypropyl, etc., a sulfoalkyl group such as sulfoethyl, sulfopropyl, etc., a 2-hydroxy-3-sulfopropyl group, etc.; and a hydroxy group.

The substituents $R^2$, $R^3$ and $R^4$ can be the same or different from each other. But it is necessary that at least one of $R^2$, $R^3$ and $R^4$ should be a substituted phenyl group having a hydroxy group or an amino group which may have one or more substituents, at the paraposition which regard to the imidazole ring.

Examples of the triarylimidazole derivatives of the formula [I] are as follows:

1-(phenylsulfonylaminocarbonyl)-2-(3,5-dimethoxy-4-hydroxyphenyl)-4,5-bis(4-diethylaminophenyl)imidazole [Compound (1)]

1-(p-toluenesulfonylaminocarbonyl)-2-(3,5-dimethoxy-4-hydroxyphenyl)-4,5-bis(4-diethylaminophenyl)imidazole [Compound (2)]

1-(p-toluenesulfonylaminocarbonyl)-2-(3,5-dimethoxy-4-hydroxyphenyl)-4,5-bis(N,N-dihydroxyethylaminophenyl)imidazole [Compound (3)]

1-(p-toluenesulfonylaminocarbonyl)-2-(3,5-dimethoxy-4-diethylaminophenyl)-4,5-bis(4-diethylaminophenyl)imidazole [Compound (4)]

1-(ethoxycarbonylaminocarbonyl)-2-(3,5-dimethoxy-4-hydroxyphenyl)-4,5-bis(4-diethylaminophenyl)imidazole [Compound (5)]

1-(p-toluenesulfonylaminocarbonyl)-2-(3,5-dimethoxy-4-hydroxyphenyl)-4,5-bis(N-ethyl-N-sulfopropylaminophenyl)imidazole 1-(aminothiocarbonyl)-2-(4-hydroxyphenyl)-4,5-bis(4-diethylamino-2-methylphenyl)imidazole [Compound (6)]

1-(ethylaminothiocarbonyl)-2-(3,5-dimethoxy-4-hydroxyphenyl)-4,5-bis(4-diethylaminophenyl)imidazole [Compound (7)]

1-(methylaminothiocarbonyl)-2-(3,5-dimethoxy-4-hydroxyphenyl)-4,5-bis{4-[bis(2-hydroxyethyl)amino]phenyl}imidazole [Compound (8)]

1-(phenylaminothiocarbonyl)-2-(4-hydroxynaphthyl)-4,5-bis{4-[N-(2-carboxyethyl)-N-ethylamino]-phenyl}imidazole [Compound (9)]

1-(p-fluorophenylaminothiocarbonyl)-2-(3,5-dimethoxy-4-hydroxyphenyl)-4,5-bis{4-[N-ethyl-N-(2-sulfonyl)amino]phenyl}imidazole [Compound (10)]

1-(ethylaminothiocarbonyl)-2-(3,5-dimethoxy-4-hydroxyphenyl)-4,5-bis(N,N-dihydroxyethylaminophenyl)imidazole The triarylimidazole derivative of the formula [I] can be synthesized as follows.

A compound of the formula:

  [II]

wherein $R^4$ is as defined above, a compound of the formula:

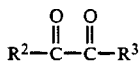  [III]

wherein $R^2$ and $R^3$ are as defined above, and ammonium acetate (or ammonia, ammonium carbonate, or the like) are reacted in an acidic solvent according to a known method (e.g. U.S. Pat. No. 3,297,710 to Silversmith) to yield an imidazole derivative of the formula:

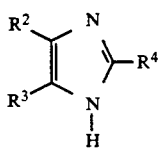  [IV]

wherein $R^2$, $R^3$ and $R^4$ are as defined above, followed by the reaction with a compound of the formula:

  [V-1]

wherein $R^1$ is as defined above, or a compound of the formula:

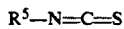  [V-2]

wherein $R^5$ is as defined above.

More concretely, one mole of the compound of the formula [II], preferably 0.2 to 1 mole, more preferably 0.5 to 0.6 mole of the compound of the formula [III] and preferably 1 to 20 moles, more preferably 2 to 10 moles of ammonium acetate, ammonium propionate, etc. are reacted in an acidic solvent such as acetic acid, propionic acid, or the like, at 100° to 150° C., preferably under reflux, for 2 to 5 hours. After purifying in a known manner, the compound of the formula [IV] is obtained. Then, one mole of the compound of the formula [IV] and preferably 1 to 10 moles, more preferably 1 to 3 moles of the compound of the formula [V-1] or [V-2] are reacted in a hydrocarbon solvent such as chloroform, dichloromethane, dichloroethane, trichloroethane, etc., at 0° to 30° C. for 1 to 72 hours, followed by a conventional purification step to yield the triarylimidazole derivative of the formula [I].

As the compound of the formula [II], there can be used commercially available phenyl aldehyde derivatives and naphthyl aldehyde derivatives. These compounds can also be obtained by formylation of a corresponding phenyl derivative or naphthyl derivative by a conventional method such as the Vilsmeier reaction.

The compound of the formula [III] can easily be obtained by reacting a corresponding phenyl derivative and/or naphthyl derivative with oxalyl chloride according to the Friedel-Craft's reaction.

As the compound of the formula [V-1], there can be used commercially available isocyanate derivatives. These isocyanate derivatives can also be obtained by the Hofmann's rearrangement using a corresponding carboxylic acid amide as a starting material.

As the compound of the formula [V-2], there can be used commercially available isothiocyanate derivatives. These isothiocyanate derivatives can also be obtained by the Hofmann's rearrangement using a corresponding thiocarboxylic acid amide as a starting material.

The triarylimidazole derivative of the formula [I] is remarkably stable in water or a buffer solution containing a surface active agent. When the triarylimidazole derivative (I) is oxidized by an oxidizing agent, e.g., oxidation by hydrogen peroxide in the presence of peroxidase, a dye which has excellent stability can be formed quantitatively.

Further, color production using the triarylimidazole derivative (I) is hardly influenced by substances present in living body samples such as serum, urine, etc., compared with the color production using the known triarylimidazole derivatives. In addition, the molecular extinction coefficient of the triarylimidazole derivative (I) is equivalent to or more than that of dyes produced from known triarylimidazole derivatives.

Therefore, the triarylimidazole derivative of the formula [I] can effectively be used as a color producing component in quantitative determination of oxidizing substances and substances which have peroxidase activity. Particularly, it can be used effectively as a color producing component in the quantitative determination of trace amount components in living body samples comprising leading hydrogen peroxide produced by an enzymatic reaction to a color producing system in the presence of substances which have peroxidase activity such as peroxidase, heme compounds such as hemoglobin, etc. and measuring the color produced colorimetrically.

The present invention also provides a process for quantitatively determining the amount of an oxidizing substance, which comprises acting a substrate or a product produced by an enzymatic reaction with an oxidase, and measuring the amount of the oxidizing substance such as hydrogen peroxide using the triarylimidazole derivative of the formula [I] as a color producing agent to determine trace amount component(s) in a living body sample.

As the trace amount components in living body samples, there can be measured cholesterol, glucose, glicerin, triglyceride, free fatty acids, uric acid, guanidine, phospholipids, bile acid, transaminase, creatine, monoamine oxidase, guanase, choline esterase, etc.

The determination of the oxidizing substance such as hydrogen peroxide using the triarylimidazole derivative (I) can be carried out according to a conventional enzymatic method (using an enzyme for generating hydrogen perodixe).

The triarylimidazole derivative of the formula [I] as a color producing agent is usually used in a concentration of 4 to 6 mole/l or more, preferably 50 to 100 μmole/l.

As the enzyme for generating hydrogen peroxide, there can be used oxidase such as cholesterol oxidase, glycerol-3-phosphate oxidase, acyl CoA-oxidase, uricase, choline oxidase, monoamineoxidase, pyruvate oxidase, sarcosine oxidase, etc.

As the substrate, there can be used cholesterol, glycerol-3-phosphate, acyl CoA, uric acid, choline, allylamine, pyruvic acid, sarcosine, etc.

As the substance which has peroxidase activity used in the determination of hydrogen peroxide, there can be used those derived from plants, animals and microorganisms. These substances which have peroxidase activity can be used alone or as a mixture thereof in amounts conventionally used.

The determination of living body components can be carried out usually at pH 4.0 to 10.0, preferably pH 6.0 to 8.0.

As the buffering agent used in the determination, there can be used conventional one such as phosphates, citrates, borates, carbonates, acetates, tris(hydroxymethyl)aminomethane, Good's buffering agent such as piperadine-N,N'-bis(2-ethanesulfonic acid) (PIPES), N-2-hydroxyethylpiperazine-N'-2-ethanesulfonic acid (HEPES), etc.

Examples of the oxidizing agent are hydrogen peroxide, periodic acid, etc.

According to the present invention, it is possible to determine the amount of substance which has peroxidase activity. Examples of the substance are peroxidase per se, heme compounds such as hemoglobin, etc.

The triarylimidazole derivative of the formula [I] can also be applied to enzyme immunoassay using peroxidaze as a labelled compound. Further, it can also be effectively used in the determination of hemoglobin in serum using an oxidizing substance such as hydrogen peroxide or sodium periodate.

In addition, the triarylimidazole derivative of the formula [I] can further be effectively used in the field of so-called dry chemistry wherein a special component in a living body fluid sample is determined by using a piece of test paper obtained by impregnating an absorptive carrier such as filter paper with a reaction reagent and drying it.

More concretely, the trace components present in living body samples can be measured as follows:

(1) Choresterol (Reactions)

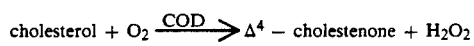

(Reagent Solution)

| 0.1M tris-maleate buffer (pH 7.0) | | |
|---|---|---|
| cholesterol esterase (CEH) | 0.1–10 u/ml | (0.3 u/ml) |
| cholesterol oxidase (COD) | 0.1–10 u/ml | (0.4 u/ml) |
| peroxidase (POD) | 0.3–30 u/ml | (5 u/ml) |
| Triton X-100 | 0.05–0.2% | (0.1%) |
| triarylimidazole derivative | 40–200 μM | (100 μM) |
| ascorbate oxidase | 3–20 u/ml | (5 u/ml) |

(Procedure)

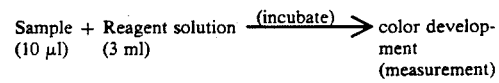

(1') Free Choresterol (Reactions)

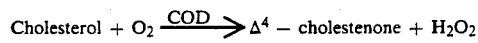

(Reagent Solution)

The same as mentioned above except for not containing CEH.

(Procedure)

The same as mentioned above (2) Glucose (Reactions)

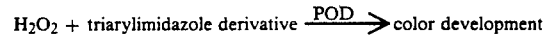

(Reagent Solution)

| 0.1M phosphate buffer (pH 7.0) | | |
|---|---|---|
| glucose oxidase (GOD) | 10–100 u/ml | (30 u/ml) |
| peroxidase (POD) | 0.3–20 u/ml | (5 u/ml) |
| triarylimidazole derivative | 50–300 μM | (100 μM) |
| [mutarotase | 0.02–0.5 u/ml | (0.067 u/ml)] |
| ascorbate oxidase (AOD) | 3–20 u/ml | (5 u/ml) |

(Procedure)

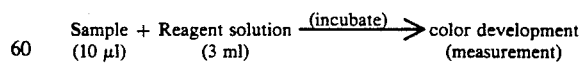

(3) Triglyceride (Reactions)

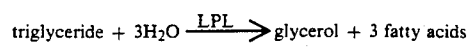

-continued glycerol + ATP $\xrightarrow{GK}$ glycerol-3-phosphate + ADP glycerol-3-phosphate + O$_2$ $\xrightarrow{GPO}$ dihydroxyacetone phosphate + H$_2$O$_2$ H$_2$O$_2$ + triarylimidazole derivative $\xrightarrow{POD}$ color development (Reagent Solution)

| tris buffer (pH 6.5) | | |
|---|---|---|
| glycerol kinase (GK) | 0.5–15 u/ml | (5 u/ml) |
| glycerol-3-phosphate oxidase (GPO) | 1–20 u/ml | (5 u/ml) |
| peroxidase (POD) | 0.3–30 u/ml | (5 u/ml) |
| magnesium acetate | 1–7 mM | (2 mM) |
| adenosine-5'-triphosphate | 0.5–30 mM | (2 mM) |
| lipoprotein lipase (LPL) | 10–150 u/ml | (60 u/ml) |
| triarylimidazole derivative | 50–300 μM | (100 μM) |
| ascorbate oxidase (AOD) | 3–20 u/ml | (5 u/ml) |

(Procedure)

Sample + Reagent solution $\xrightarrow{\text{(incubate)}}$ color development (measurement)
(10 μl)    (3 ml)

(3') Glycerol (Reactions)

glycerol + ATP $\xrightarrow{GK}$ glycerol-3-phosphate + ADP glycerol-3-phosphate + O$_2$ $\xrightarrow{GPO}$ dihydroxyacetone phosphate + H$_2$O$_2$ H$_2$O$_2$ + triarylimidazole derivative $\xrightarrow{POD}$ color development (Reagent Solution)

The same as mentioned above except for not containing LPL.

(Procedure)

The same as mentioned above (4) Non-esterified fatty acid (Reactions)

RCOOH + ATP + CoA $\xrightarrow{ACS}$ Arcyl—CoA—AMP + PPI

Arcyl—CoA + O$_2$ $\xrightarrow{ACOD}$ 2,3-trans-Enoyl-CoA + H$_2$O$_2$

H$_2$O$_2$ + triarylimidazole derivative $\xrightarrow{POD}$ color development (Reagent Solution)

| PIPES-NaOH buffer (pH 6.9) | | |
|---|---|---|
| acryl CoA-synthesizer (ACS) | 0.05–5 u/ml | (0.1 u/ml) |
| acryl CoA-oxidase (A COD) | 1–15 u/ml | (3 u/ml) |
| coenzyme A (CoA) | 0.2–5 mg/ml | (0.5 mg/ml) |
| Peroxidase (POD) | 0.3–30 u/ml | (5 u/ml) |
| ascorbate oxidase (AOD) | 3–20 u/ml | (5 u/ml) |
| triarylimidazole derivative | 40–200 mM | (100 mM) |
| adenosine-5'-phosphate (ATP) | 1–15 mg/ml | (3 mg/ml) |
| magnesium chloride | 0.5–5 mM | (2 mM) |
| Emulgen 913 (polyoxyethylene nonyl phenol ether) | 0.05–0.4% | (0.2%) |

(Procedure)

Sample + Reagent solution $\xrightarrow{\text{(incubate)}}$ color development (measurement)
(20 μl)    (3 ml)

(5) Uric Acid (Reactions)

uric acid + O$_2$ + 2H$_2$O $\xrightarrow{uricase}$ allantoin + CO$_2$ + H$_2$O$_2$ H$_2$O$_2$ + triarylimidazole derivative $\xrightarrow{POD}$ color development (Reagent Solution)

| PIPES-NaOH buffer (pH 6.4) | | |
|---|---|---|
| uricase | 0.5–10 u/ml | (2 u/ml) |
| peroxidase (POD) | 0.3–30 u/ml | (10 u/ml) |
| ascorbate oxidase (AOD) | 1–20 u/ml | (2 u/ml) |
| triarylimidazole derivative | 20–300 μM | (50 μM) |

(Procedure)

Sample + Reagent solution $\xrightarrow{\text{(incubate)}}$ color development (measurement)
(10 μl)    (3 ml)

(6) Phospholipids (Reactions)

phospholipids $\begin{pmatrix} \text{lecithin} \\ \text{sphingosine} \\ \text{lysolecithin} \end{pmatrix}$ + H$_2$O $\xrightarrow{\text{phospholipase}}$ choline + $\begin{pmatrix} \text{phosphatidic acid} \\ \text{N-acylsphingosyl phosphate} \\ \text{lysophosphatidic acid} \end{pmatrix}$ choline $\xrightarrow{\text{choline oxidase}}$ betaine + 2H$_2$O$_2$ H$_2$O$_2$ + triarylimidazole derivative $\xrightarrow{POD}$ color development (Reagent Solution)

| tris buffer (pH 7.7) | | |
|---|---|---|
| phospholipase D | 0.4–10 u/ml | (0.7 u/ml) |
| choline oxidase | 1–20 u/ml | (3 u/ml) |

-continued

| | | |
|---|---|---|
| peroxidase (POD) | 0.3-30 u/ml | (5 u/ml) |
| ascorbate oxidase | 2-20 u/ml | (5 u/ml) |
| triarylimidazole derivative | 50-300 μM | (100 μM) |

(Procedure)

Sample + Reagent solution $\xrightarrow{\text{(incubate)}}$ color development
(10 μl) (3 ml) (measurement)

(7) Monoamine oxidase (MAO)

(Reactions)

$CH_2=CHCH_2NH_2 + O_2 + H_2O \xrightarrow{MAO}$
(allylamine)

$CH_2=CHCHO + NH_3 + H_2O_2$
(acrolein)

$H_2O_2$ + triarylimidazole derivative $\xrightarrow{POD}$ color development (Reagent Solution)

| | | |
|---|---|---|
| 25 mM PIPES-NaOH buffer (pH 6.75) | | |
| allylamine | 10-100 mM | (25 mM) |
| peroxidase (POD) | 0.3-30 u/ml | (5 u/ml) |
| ascorbate oxidase | 2-20 u/ml | (5 u/ml) |
| triarylimidazole derivative | 5-100 μM | (30 μM) |

(Procedure)

Sample + Reagent solution ⟶ rate assay
(100 μl) (3 ml) (incubate)

(8) Transaminase (A) Glutamic oxaloacetic transaminase (GOT)

L-aspartic acid + α-ketoglutaric acid $\underset{\longrightarrow}{\xleftarrow{GOT}}$ oxaloacetic acid + glutamic acid oxaloacetic acid $\xrightarrow{OAC}$ pyruvic acid + $CO_2$ (B) Glutamic Pyruvic Transaminase L-alanine + α-ketoglutaric acid $\underset{\longrightarrow}{\xleftarrow{GPT}}$ pyruvic acid + glutamic acid pyruvic acid + $HOPO_3^{2-}$ + $O_2$ $\xrightarrow{POP}$ acetyl phosphate + $CO_2$ + $H_2O_2$ -continued $H_2O_2$ + triarylimidazole derivative $\xrightarrow{POD}$ color development (Reagent Solution)

(A) GPT

First Solution

| | | |
|---|---|---|
| phosphate buffer (pH 7.0) | | |
| pyruvate oxidase (POP) | 1-10 u/ml | (6 u/ml) |
| peroxidase (POD) | 0.2-20 u/ml | (10 u/ml) |
| thiamine pyrophosphate (TPP) | 0.01-0.5% | (0.06%) |
| flavin-adenine dinucleotide (FAD) | 0.001-0.1% | (0.002%) |
| magnesium acetate | 1-10 mM | (9 mM) |
| catalase | 50-500 u/ml | (100 u/ml) |

Second Solution

| | | |
|---|---|---|
| phosphate buffer (pH 7.0) | | |
| DL-alanine | 200-800 mM | (700 mM) |
| α-ketoglutamic acid | 10-50 mM | (35 mM) |
| triarylimidazole derivative | 20-300 μM | (50 μM) |
| $NaN_3$ | 0.1-0.4% | (0.2%) |

Third Solution (Reaction Stopper)

| | | |
|---|---|---|
| 0.1M citrate buffer (pH 6.8) | | |
| sodium dodecylbenzenesulfonate | 0.1-1% | (0.5%) |
| EDTA.2Na | 0.5-2 mM/l | (1 mM/l) |

(Procedure)

Sample + 1st reagent solution $\xrightarrow[\text{(37° C., 5 min)}]{\text{(incubate)}}$ +
(20 μl) (0.5 ml)

2nd reagent solution $\xrightarrow[\text{(37° C., 20 min)}]{\text{(incubate)}}$ +
(0.5 ml)

reaction stopper ⟶ color development
(2 ml) (measurement)

(B) GOT

First Solution

| | | |
|---|---|---|
| Phosphate buffer (pH 7.0) | | |
| pyruvate oxidase (POP) | 1-10 u/ml | (6 u/ml) |
| peroxidase (POD) | 0.2-20 u/ml | (10 u/ml) |
| thiamine pyrophosphate (TPP) | 0.01-0.5% | (0.06%) |
| flavin-adenine dinucleotide (FAD) | 0.001-0.1% | (0.002%) |
| magnesium acetate | 1-10 mM | (9 mM) |
| catalase | 50-500 u/ml | (100 u/ml) |
| oxaloacetate decarboxylase (OAC) | 1-50 u/ml | (20 u/ml) |

Second Solution

| | | |
|---|---|---|
| phosphate buffer (pH 7.0) | | |
| L-aspartic acid | 100-600 mM | (400 mM) |
| α-ketoglutaric acid | 10-50 mM | (35 mM) |

-continued

| | | |
|---|---|---|
| triarylimidazole derivative | 20–300 μM | (50 μM) |
| NaN$_3$ | 0.1–0.4% | (0.2%) |

Third Solution (Reaction Stopper)

| | | |
|---|---|---|
| 0.1M citrate buffer (pH 6.8) | | |
| sodium dodecyl-benzenesulfonate | 0.1–1% | (0.5%) |
| EDTA.2Na | 0.5–2 mM/l | (1 mM/l) |

(Procedure)

Sample + 1st reagent solution $\xrightarrow[(37° C., 5 min)]{(incubate)}$ +
(20 μl)   (0.5 ml)

2nd reagent solution $\xrightarrow[(37° C., 20 min)]{(incubate)}$ +
(0.5 ml)

reaction stopper $\longrightarrow$ color development
(2 ml)   (measurement)

(9) Creatine (Reactions)

creatine + H$_2$O $\xrightarrow{\text{creatine amidinohydrase}}$ sarcosine + urea sarcosine + H$_2$O + O$_2$ $\xrightarrow{\text{sarcosine oxidase}}$ H$_2$O$_2$ + HCHO + glycine H$_2$O$_2$ + triarylimidazole derivative $\xrightarrow{\text{POD}}$ color development (Reagent Solution)

First Solution

| | | |
|---|---|---|
| 50 mM phosphate buffer (pH 8.0) | | |
| sarcosine oxidase | 1–40 u/ml | (20 u/ml) |
| peroxidase | 0.2–20 u/ml | (10 u/ml) |
| catalase | 50–400 u/ml | (100 u/ml) |

Second Solution

| | | |
|---|---|---|
| 50 mM phosphate buffer (pH 8.0) | | |
| creatine amidinohydrase | 1–100 u/ml | (50 u/ml) |
| NaN$_3$ | 0.1–0.4% | (0.2%) |
| triarylimidazole derivative | 30–400 μM | (50 μM) |

(Procedure)

Sample + 1st reagent solution $\xrightarrow[(37° C., 5 min)]{(incubate)}$ +
(50 μl)   (1 ml)

2nd reagent solution $\xrightarrow[(37° C., 5–10 min)]{(incubate)}$ color development
(1 ml)   (measurement)

(10) Bile Acids (Reactions)

3α-hydroxysteroid + NAD$^+$ $\xrightarrow{\text{3α-HSD}}$ 3-ketosteroid + NADH + H$^+$ NADH + triarylimidazole derivative $\xrightarrow[\text{Mn}^{2+}]{\text{POD}}$ color development (Reagent Solution)

| | | |
|---|---|---|
| 50 mM tris-HCl buffer (pH 8.0) | | |
| 3α-hydroxysteroid dehydrogenase (3α-HSD) | 0.005–1 u/ml | (0.01 u/ml) |
| nicotinamide adenine dinucleotide (NAD) | 0.1–3 mM | (1 mM) |
| MnCl$_2$ | 0.2–5 mM | (1 mM) |
| peroxidase (POD) | 0.2–30 u/ml | (3 u/ml) |
| triarylimidazole derivative | 30–300 μM | (50 μM) |

(Procedure)

Sample + Reagent solution $\xrightarrow[(37° C., 20 min)]{(incubate)}$
(50 μl)   (3 ml)

color development
(measurement)

(11) Peroxidase (Reaction)

triarylimidazole derivative + H$_2$O$_2$ $\xrightarrow{\text{POD}}$
(substrate)

color development (Reagent Solution)

| | | |
|---|---|---|
| 50 mM phosphate buffer (pH 6.0) | | |
| triarylimidazole derivative | 30–300 μM | (50 μM) |
| H$_2$O$_2$ | 0.02–0.3 mM | (0.1 mM) |

(Procedure)

Sample + Reagent solution $\xrightarrow{\text{(incubate)}}$ color development
(10 μl)   (3 ml)   (measurement)

The POD activity can be obtained by measuring a changing rate per unit time. This procedure can also be applied to the determination of hemoglobin.

The present invention is illustrated by way of the following Examples, in which all percents are by weight, unless otherwise specified.

EXAMPLE 1

Synthesis of
1-(p-toluenesulfonylaminocarbonyl)-2-(3,5-dimethoxy-4-hydroxyphenyl)-4,5-bis(4-diethylaminophenyl)imidazole [Compound (2)]

(1) Synthesis of
1,2-bis(4-diethylaminophenyl)ethane-1,2-dione

To 11.6 g of anhydrous aluminum chloride, 60 ml of carbon disulfide was added, followed by dropwise addition of 30 g of N,N-diethylaniline under ice-cooling. Then, 10 g of oxalyl chloride was added dropwise thereto at 5° C. or lower, followed by the reaction for 1 hour with stirring. After the reaction, the reaction solution was poured into 100 ml of water and 200 ml of chloroform. The chloroform layer obtained by separation was washed with 2N hydrochloric acid, dried and concentrated. The residue was recrystallized from ethyl acetate to give yellow 1,2-bis(4-diethylaminophenyl)ethane-1,2-dione in an amount of 7.0 g.

(2) Synthesis of
2-(3,5-dimethoxy-4-hydroxyphenyl)-4,5-bis(4-diethylaminophenyl)imidazole In 100 g of acetic acid, 7.0 g of 1,2-bis(4-diethylaminophenyl)ethane-1,2-dione obtained in above (1), 3.6 g of syringaaldehyde (mfd. by tokyo Kasei Kogyo Co., Ltd.) and 4 g of ammonium acetate were reacted under reflux for 5 hours. After the reaction, 600 ml of water was poured into the reaction solution. The produced viscous residue was separated and the viscous residue was purified by silica gel chromatography (eluent: a mixed solvent of chloroform and methanol) to give 1.6 g of 2-(3,5-dimethoxy-4-hydroxyphenyl)-4,5-bis(4-diethylaminophenyl)imidazole.

(3) Synthesis of Compound (2)

In 20 ml of chloroform, 0.8 g of 2-(3,5-dimethoxy-4-hydroxyphenyl)-4,5-bis(4-diethylaminophenyl)imidazole obtained in above (2) was dissolved. After adding 1 g of p-toluenesulfonyl isocyanate (mfd. by Wako Pure Chemical Industries, Ltd.) to the resulting solution, the reaction was carried out at room temperature for 5 hours with stirring. After the reaction, 5 ml of methanol was poured into the reaction solution to decompose excess n-toluenesulfonyl isocyanate, followed by removal of the solvent by distillation under reduced pressure. The obtained oily residue was purified by silica gel column chromatography (eluent: a mixed solvent of ethyl acetate and n-hexane) to give 0.7 g of dark green crystals of 1-(p-toluenesulfonylaminocarbonyl)-2-(3,5-dimethoxy-4-hydroxyphenyl)-4,5-bis(4-diethylaminopheny)imidazole having a m.p. of 65° C.

IR: 3400 cm$^{-1}$ (OH), 2800–3000 cm$^{-1}$ (CH), 1720 cm$^{-1}$ (C=O), 1600 cm$^{-1}$ (aromatic CH), 1500 cm$^{-1}$ (aromatic CH).

Elementary analysis ($C_{39}H_{45}N_5O_6S$)

|  | C | H | N |
|---|---|---|---|
| Calcd. (%) | 65.74 | 6.37 | 9.84 |
| Found (%) | 65.34 | 6.10 | 9.72 |

EXAMPLE 2

Using 1,2-bis(4-diethylaminophenyl)ethane-1,2-dione and N,N-diethyl-2,6-dimethoxy-4-formylaniline as starting materials, the reaction and aftertreatment were carried out in the same manner as described in Example 1 (2) to synthesize 2-(3,5-dimethoxy-4-diethylaminophenyl)-4,5-bis(4-diethylaminophenyl)imidazole.

The resulting compound and p-toluenesulfonyl isocyanurate as starting materials were reacted and after-treated in the same manner as described in Example 1 (3), 0.8 g of 1-(p-toluenesulfonylaminocarbonyl)-2-(3,5-dimethoxy-diethylaminophenyl)-4,5-bis(4-diethylaminophenyl)imidazole [Compound (4)] was obtained.

EXAMPLE 3

Synthesis of
1-(ethoxycarbonylaminocarbonyl)-2-(3,5-dimethoxy-4-hydroxyphenyl)-4,5-bis(4-diethylaminophenyl)imidazole [Compound (5)]

In 20 ml of chloroform, 0.8 g of 2-(3,5-dimethoxy-4-hydroxyphenyl)-4,5-bis(4-diethylaminophenyl)imidazole obtained in Example 1 (2) was dissolved. Then, 0.7 g of ethoxycarbonyl isocyanate (mfd. by Aldrich Chemical Co. Inc.) was added to the resulting solution and the reaction was carried out at room temperature for 5 hours with stirring. After the reaction, 5 ml of methanol was added to the reaction solution to decompose excess ethoxycarbonyl isocyanate, followed by removal of the solvent by distillation under reduced pressure. The obtained residue was purified by silica gel column chromatography (eluent: a mixed solvent of ethyl acetate and n-hexane) to give 0.6 g of green crystals of 1-(ethoxycarbonylaminocarbonyl)-2-(3,5-dimethoxy-4-hydroxyphenyl)-4,5-bis(4-diethylaminophenyl)imidazol having a m.p. of 60° C.

IR: 3400 cm$^{-1}$ (OH), 2800–3000 cm$^{-1}$ (CH), 1735 cm$^{-1}$ (C=O), 1720 cm$^{-1}$ (C=O), 1600 cm$^{-1}$ (aromatic CH), 1500 cm$^{-1}$ (aromatic CH).

Elementary analysis ($C_{35}H_{43}N_5O_6$)

|  | C | H | N |
|---|---|---|---|
| Calcd. (%) | 66.75 | 6.88 | 11.12 |
| Found (%) | 66.09 | 6.60 | 10.80 |

EXAMPLE 4

Using 2-(3,5-dimethoxy-4-hydroxyphenyl)-4,5-bis(4-diethylaminophenyl)imidazole and phenylsulfonyl isocyanate as starting materials, the reaction and aftertreatment were carried out in the same manner as described in Example 3 to give 1.2 g of 1-(phenylsulfonylaminocarbonyl)-2-(3,5-dimethoxy-4-hydroxyphenyl)-4,5-bis(4-diethylaminophenyl)imidazole [Compound (1)].

EXAMPLE 5

Measurements of various properties of triarylimidazole derivatives (I)

(1) Measurement of Molecular Extinction Coefficient and Maximum Absorption (λmax)

(Color Developing Solution)

A color developing solution was prepared by dissolving a triarylimidazole derivative of the formula (I) in an amount of 0.5 mM and peroxidase so as to make the content 4 U/ml in 50 mM of piperazine-N,N'-bis(2-ethanesulfonic acid) (PIPES) - sodium hydroxide buffer solution (pH 7.0).

(Procedures)

To 3 ml of a color developing solution thus prepared, 20 μl of 1 mM aqueous hydrogen peroxide was added and mixed well, followed by heating at 37° C. for 5 minutes. The reaction solution was subjected to measurement of absorption curve to provide λ max and absorbance $E_S$ at λ max.

As a control for obtaining the absorption curve and λ max, there was used one obtained by adding 20 μl of purified water to 3 ml of each color developing solution, and mixing well, followed by heating at 37° C. for 5 minutes.

The molecular extinction coefficient was obtained by using the $E_S$ obtained by using each color developing solution as mentioned above, and absorbance $E_{OH}$ at 505 nm obtained by using 50 mM PIPES - sodium hydroxide buffer solution (pH 7.0) containing 50 mM of 4-aminoantipyrine, 50 mM of phenol and 4 U/ml of peroxidase in place of each color developing solution in the same manner as described in the above-mentioned "Procedures".

Molecular extinction coefficient $= (E_S/E_{OH}) \times 5 \times 10^3$

The results are shown in Table 1.

(2) Measurement of Influences of Serum Components

To 3 ml of a color developing solution prepared in above (1), 20 μl of normal human serum was added and mixed. Then, 20 μl of 1 mM of aqueous hydrogen peroxide was added to the resulting solution and mixed, followed by reaction at 37° C. for 5 minutes. Absorbance $E_{ef}$ of the reaction solution at λ max was measured. Further, using purified water in place of the normal human serum, absorbance $E_{std}$ was obtained using the same color developing solution and the same procedure mentioned above.

An index "a" value for evaluating influences of serum components was obtained from the following equation using $E_{ef}$ and $E_{std}$ obtained above:

$$a = (E_{std} - E_{ef}/E_{std}) \times 100$$

Influences of serum components were evaluated as follows:
−: a is 0 to 3
±: a is 3 to 6
++: a is 20 or more The results are also shown in Table 1.

In Table 1, the same properties of known triarylimidazole derivatives were also measured for comparison and listed in Table 1.

TABLE 1

| Compound No. | R¹ | R² | R³ | R⁴ | Molecular extinction coefficient ($\times 10^3$) | $\lambda$ max (nm) | Influences of serum component |
|---|---|---|---|---|---|---|---|
| Compounds of the present invention | | | | | | | |
| 1 | C₆H₅—SO₂— | 4-(C₂H₅)₂N—C₆H₄— | 4-(C₂H₅)₂N—C₆H₄— | 3,5-(H₃CO)₂-4-HO—C₆H₂— | 50 | 660 | — |
| 2 | 4-H₃C—C₆H₄—SO₂— | 4-(C₂H₅)₂N—C₆H₄— | 4-(C₂H₅)₂N—C₆H₄— | 3,5-(H₃CO)₂-4-HO—C₆H₂— | 50 | 660 | — |
| 3 | H₇C₃—SO₂— | 4-HO—C₆H₄— | 4-(C₂H₅)₂N—C₆H₄— | 3,5-(H₃CO)₂-4-HO—C₆H₂— | 32 | 620 | — |
| 4 | 4-H₃C—C₆H₄—SO₂— | 4-(C₂H₅)₂N—C₆H₄— | 4-(C₂H₅)₂N—C₆H₄— | 3,5-(H₃CO)₂-4-(C₂H₅)₂N—C₆H₂— | 50 | 840 | — |
| Comparison | | | | | | | |
| 5 | H₅C₂O—CO— | 4-(C₂H₅)₂N—C₆H₄— | 4-(C₂H₅)₂N—C₆H₄— | 3,5-(H₃CO)₂-4-HO—C₆H₂— | 50 | 660 | ± |

TABLE 1-continued

| Compound No. | R¹ | R² | R³ | R⁴ | Molecular extinction coefficient ($\times 10^3$) | $\lambda$ max (nm) | Influences of serum component |
|---|---|---|---|---|---|---|---|
| 1 | | (C₂H₅)₂N–C₆H₄– , (C₂H₅)₂N–C₆H₄– (on ring with N, NH; R³ = 4-HO–C₆H₄–) | | | 32 | 620 | ++ |
| 2 | | (C₂H₅)₂N–C₆H₄– , (C₂H₅)₂N–C₆H₄– (on ring with N, N–CONHC₂H₅; R³ = 4-(CH₃)₂N–C₆H₄–) | | | 25 | 820 | ++ |

As is clear from the results of Table 1, the triarylimidazole derivatives of the formula (I) are equal to or larger than the known triarylimidazole derivatives in the molecular extinction coefficient. But undesirable influences of components contained in the living body samples such as serum are not shown in the case of the triarylimidazole derivatives of the present invention in contrast to the known triarylimidazole derivatives.

EXAMPLE 6

Determination of Hydrogen Peroxide (Measuring Solution)

A measuring solution was prepared by dissolving the following reagents in 50 mM PIPES - sodium hydroxide buffer solution (pH 7.0):

| | |
|---|---|
| Compound (2) | 0.5 mM |
| Peroxidase | 4 U/ml |

(Sample)

Samples were prepared by diluting commercially available aqueous hydrogen peroxide with distilled water to give solutions of 0.5, 1.0, 1.5, 2.0 and 4.0 mM.

(Procedure)

To 3 ml of a measuring solution, 20 μl of a sample was added and mixed well, followed by heating at 37° C. for 5 minutes. Then absorbance ($E_S$) at 660 nm was measured.

Further, using deionized water in place of the sample, a blank value ($E_{B1}$) was measured in the same manner as mentioned above.

(Results)

Measured results are shown in FIG. 1.

As is clear from FIG. 1, the calibration curve obtained by lining plotted points as to the absorbance ($E_S$-$E_{B1}$) taken along the ordinate axis and the hydrogen peroxide concentration taken along the abscissa axis shows good linearity. Therefore, hydrogen peroxide can be determined quantitatively by the process according to the present invention.

The same results were obtained when Compounds (1), (3), (4) and (5) of the present invention were used in place of Compound (2).

EXAMPLE 7

Determination of Hydrogen Peroxide in the Presence of Serum Components (Measuring Solution)

The same as Example 6.

(Sample)

The same as Example 6.

(Procedure)

To 3 ml of a measuring solution, 50 μl of normal human serum or deionized water was added and mixed well. Then, 20 μl of a sample was added to the resulting solution and mixed, followed by heating at 37° C. for 5 minutes. Subsequently, absorbance ($E_S$) at 660 nm was measured.

Using deionized water in place of the sample, a blank value ($E_{B1}$) was measured in the same manner as mentioned above.

(Results)

Measured results are shown in Table 2.

TABLE 2

| $H_2O_2$ concentration in sample (mM) | $E_S - E_{B1}$ In the presence of normal human serum | $E_S - E_{B1}$ In the presence of deionized water |
|---|---|---|
| 0.5 | 0.184 | 0.187 |
| 1.0 | 0.377 | 0.381 |
| 1.5 | 0.561 | 0.570 |
| 2.0 | 0.749 | 0.758 |
| 4.0 | 1.501 | 1.521 |

As is clear from Table 2, when the triarylimidazole derivative of the present invention is used, the dye produced therefrom is hardly influenced by the serum components irrespective of the hydrogen peroxide concentration.

EXAMPLE 8

Determination of Uric Acid (Measuring Solution)

A measuring solution was prepared by dissolving the following reagents in 50 mM PIPES - sodium hydroxide buffer solution (pH 7.0):

| | |
|---|---|
| Compound (2) | 0.05 mM |
| Peroxidase | 4 U/ml |
| Uricase | 0.05 U/ml |

(Sample)

Five samples of standard solutions containing 10 mg/dl of uric acid and human serum were prepared.

(Procedure)

To 3 ml of a measuring solution, 20 μl of a sample was added, mixed well, and heated at 37° C. for 5 minutes, followed by measurement of absorbance ($E_S$) at 660 nm.

Further, using deionized water in place of the sample, a blank value ($E_{B1}$) was measured in the same manner as mentioned above.

Concentration of uric acid in human serum was calculated by the following equation:

$$\text{Uric acid (mg/dl)} = \frac{E_S - E_{B1} \text{ of human serum}}{E_S - E_{B1} \text{ of standard solution}} \times 10$$

(Results)

The results are shown in Table 3.

Reference Example 1

Determination of Uric Acid

Using the same samples as used in Example 8 and commercially available kit for measuring uric acid (Uric acid C-Test Wako, a trade name, mfd. by Wako Pure Chemical Industries, ltd.), uric acid concentrations were measured.

The results are also shown in Table 3.

TABLE 3

| Human serum No. | Uric acid values (mg/dl) | |
|---|---|---|
| | Example 8 | Reference Example 1 |
| 1 | 3.9 | 3.9 |
| 2 | 4.5 | 4.5 |
| 3 | 5.7 | 5.8 |
| 4 | 6.3 | 6.5 |
| 5 | 8.4 | 8.5 |

As is clear from Table 3, the measured values of uric acid obtained by the method of Example 8 using the triarylimidazole derivative of the present invention as a color producing component show good correlation with those obtained by using the commercially available kit.

EXAMPLE 9

Synthesis of 1-(aminothiocarbonyl)-2-(4-hydroxyphenyl)-4,5-bis(4-diethylamino-2-methylphenyl)imidazole [Compound (6)]

(1) Synthesis of 1,2-bis(4-diethylamino-2-methylphenyl)ethane-1,2-dione

To 8.3 g of anhydrous aluminum chloride, 30 ml of carbon disulfide was added, followed by dropwise addition of 16.3 g of N,N-diethyl-m-toluidine under ice-cooling. Then, 5 g of oxalyl chloride was added dropwise thereto at 5° C. or lower, and reacted for 1 hour with stirring. After the reaction, 50 ml of water and 100 ml of chloroform were added to the reaction solution. The chloroform layer obtained by separation was washed with 2N hydrochloric acid, dried and concentrated. The residue was recrystallized from ethyl acetate to yield 3.5 g of yellow 1,2-bis(4-diethylamino-2-methylphenyl)ethane-1,2-dione.

(2) Synthesis of Compound (6)

In 50 g of acetic acid, 3.5 g of 1,2-bis(4-diethylamino-2-methylphenyl)ethane-1,2-dione, 1.2 g of 4-hydroxybenzaldehyde (mfd. by Wako Pure Chemical Industries, Ltd.) and 2 g of ammonium acetate were reacted under reflux for 3 hours. After the reaction, 300 ml of water was added to the reaction solution and the resulting viscous residue was separated. The viscous residue was purified by silica gel column chromatography (eluent: a mixed solvent of chloroform and methanol) to give 0.9 g of 2-(4-hydroxyphenyl)-4,5-bis(4-diethylamino-2-methylphenyl)imidazole.

Then, the resulting compound was dissolved in 20 ml of chloroform. To the resulting solution, 3 g of ethoxycarbonyl isothiocyanate (mfd. by Aldrich Chemical Co. Inc.) was added and reacted at room temperature for 24 hours with stirring. After the reaction, 5 ml of methanol was added to the reaction solution to decompose excess ethoxycarbonyl isothiocyanate, followed by removal of the solvent by distillation under reduced pressure. The obtained residue was purified by silica gel column chromatography (eluent: a mixed solution of ethyl acetate and n-hexane) to give 1-[(ethoxycarbonylamino)thiocarbonyl]-2-(4-hydroxyphenyl)-4,5-bis(4-diethylamino-2-methylphenyl)imidazole. The resulting compound was dissolved in 20 ml of methanol, and saponified by adding 2 ml of 1N NaOH, followed by neutralization of the reaction solution with 1N HCl. The reaction solution was concentrated to dryness. The resulting residue was purified again by silica gel column chromatography (eluent: a mixed solvent of ethyl acetate and n-hexane) to give 0.5 g of pale green crystals of 1-(aminothiocarbonyl)-2-(4-hydroxyphenyl)-4,5-bis(4-diethylamino-2-methylphenyl)imidazole.

IR: 3400 cm$^{-1}$ (OH), 2800–3000 cm$^{-1}$ (aliphatic CH), 1200 cm$^{-1}$ (C=S), 1600 cm$^{-1}$ (aromatic CH), 1500 cm$^{-1}$ (aromatic CH).

Elementary analysis ($C_{32}H_{39}N_5OS$)

| | C | H | N |
|---|---|---|---|
| Calcd. (%) | 70.95 | 7.26 | 12.93 |
| Found (%) | 70.60 | 7.01 | 12.55 |

EXAMPLE 10

Synthesis of 1-(ethylaminothiocarbonyl)-2-(3,5-dimethoxy-4-hydroxyphenyl)-4,5-bis(4-diethylaminophenyl)imidazole [Compound (7)]

(1) Synthesis of 1,2-bis(4-diethylaminophenyl)ethane-1,2-dione

To 5.8 g of anhydrous aluminum chloride, 30 ml of carbon disulfide was added, followed by dropwise addition of 15 g of N,N-diethylaniline under ice-cooling to carry out the reaction for 1 hour with stirring. After pouring water into the reaction solution, the desired compound was extracted with chloroform. The extracted solution was washed with 2N HCl, dried and concentrated. The residue was recrystallized from ethyl acetate to give 3.3 g of yellow 1,2-bis(4-diethylaminophenyl)ethane-1,2-dione.

(2) Synthesis of Compound (7)

In 50 g of acetic acid, 3.3 g of 1,2-bis(4-diethylaminophenyl)ethane-1,2-dione, 1.2 g of syringaaldehyde (mfd. by Tokyo Kasei Kogyo Co., Ltd.) and 2 g of ammonium acetate were reacted under reflux for 3 hours. After the reaction, 300 ml of water was poured into the reaction solution. The produced viscous residue was separated and purified by silica gel column chromatography (eluent: a mixed solvent of chloroform and methanol) to give 0.8 g of 2-(3,5-dimethoxy-4-hydroxyphenyl)-4,5-bis(4-diethylamino)imidazole.

Then, the resulting compound was dissolved in 20 ml of chloroform and 10 g of ethyl isothiocyanate (mfd. by Wako Pure Chemical Industries, Ltd.) was added thereto. The reaction was carried out at room temperature for 48 hours. After the reaction, 30 ml of methanol was poured into the reaction solution to decompose excess ethyl isothiocyanate. Then, the solvent was removed by distillation under reduced pressure. The obtained residue was purified by silica gel column chromatography (eluent: a mixed solvent of ethyl acetate and n-hexane) to give 0.8 g of pale green crystals of 1-(ethylaminothiocarbonyl)-2-(3,5-dimethoxy-4-hydroxyphenyl)-4,5-bis(4-diethylaminophenyl)imidazole.

IR: 3400 cm$^{-1}$ (OH), 2800–3000 cm$^{-1}$ (aliphatic CH), 1200 cm$^{-1}$ (C=S), 1600 cm$^{-1}$ (aromatic CH), 1500 cm$^{-1}$ (aromatic CH).

Elementary analysis ($C_{24}H_{43}N_5O_3S$)

| | C | H | N |
|---|---|---|---|
| Calcd. (%) | 59.85 | 9.00 | 14.54 |

-continued

| | C | H | N |
|---|---|---|---|
| Found (%) | 59.25 | 8.70 | 14.14 |

EXAMPLES 11 to 13

Using 1,2-bis{4-[bis(2-hydroxyethyl)amino]phenyl}ethane-1,2-dione, syringaaldehyde and methyl isothiocyanate as starting materials, the reaction and aftertreatment were carried out in the same manner as Example 9 to yield 1.1 g of 1-(methylaminothiocarboxyl)-2-(3,5-dimethoxy-4-hydroxyphenyl)-4,5-bis{4-[bis(2-hydroxyethyl)amino]phenyl}imidazole [Compound (8)].

In the same manner as mentioned above, 1.0 g of 1-(phenylaminothiocarbonyl)-2-(4-hydroxynaphthyl)-4,5-bis{4-[N-(2-carboxyethyl)-N-ethylamino]phenyl}-imidazole [Compound (9)] was obtained by using 1,2-bis{4-[N-(2-carboxyethyl)-N-ethylamino]phenyl}ethane-1,2-dione, 4-formyl-1-naphthol and phenyl isothiocyanate as starting materials.

Further, 1.2 g of 1-(p-fluorophenylaminothiocarbonyl)-2-(3,5-dimethoxy-4-hydroxyphenyl)-4,5-bis{4-[N-ethyl-N-(2-sulfoethyl)amino]phenyl}imidazole [Compound (10)] was obtained in the same manner as described above using 1,2-bis{4-[N-ethyl-N-(2-sulfonylethyl)amino]phenyl}ethane-1,2-dione, syringaaldehyde and p-fluorophenyl isothiocyanate as starting materials.

EXAMPLE 16

Measurements of Various Properties of Triarylimidazole Derivatives (I)

(1) Measurement of Molecular Extinction Coefficient and Maximum Absorption ($\lambda$ max)

(Color Developing Solution)

The same as Example 5

(Procedures)

The same as Example 5.
The results are shown in Table 4.

(2) Measurement of influences of serum components

The same as Example 5.
The results are shown in Table 4.

In Table 4, the same properties of known triarylimidazole derivatives were also measured for comparison and listed in Table 4.

TABLE 4

| Compound No. | $R^5$ | $R^2$ | $R^3$ | $R^4$ | Molecular extinction coefficient ($\times 10^3$) | $\lambda$ max (nm) | Influences of serum components |
|---|---|---|---|---|---|---|---|
| *Compounds of the present invention* | | | | | | | |
| 6 | H | (C$_2$H$_5$)$_2$N—⟨⟩—CH$_3$ | (C$_2$H$_5$)$_2$N—⟨⟩—CH$_3$ | HO—⟨⟩— | 40 | 675 | — |
| 7 | H$_5$C$_2$— | (C$_2$H$_5$)$_2$N—⟨⟩— | (C$_2$H$_5$)$_2$N—⟨⟩— | H$_3$CO—⟨⟩(OH)—OCH$_3$ | 49 | 660 | — |
| 8 | H$_3$C— | (HOH$_4$C$_2$)$_2$N—⟨⟩— | (HOH$_4$C$_2$)$_2$N—⟨⟩— | H$_3$CO—⟨⟩(OH)—OCH$_3$ | 46 | 660 | — |
| 9 | ⟨⟩— | (HOOCH$_4$C$_2$)(H$_5$C$_2$)N—⟨⟩— | (HOOCH$_4$C$_2$)(H$_5$C$_2$)N—⟨⟩— | HO—naphthyl | 40 | 650 | ± |
| 10 | F—⟨⟩— | (HO$_3$SH$_4$C$_2$)(H$_5$C$_2$)N—⟨⟩— | (HO$_3$SH$_4$C$_2$)(H$_5$C$_2$)N—⟨⟩— | H$_3$CO—⟨⟩(OH)—OCH$_3$ | 40 | 660 | — |
| *Comparison* | | | | | | | |

TABLE 4-continued

| Compound No. | R⁵ | R² | R³ | R⁴ | Molecular extinction coefficient (× 10³) | λ max (nm) | Influences of serum components |
|---|---|---|---|---|---|---|---|
| 1 | | (C₂H₅)₂N–C₆H₄– | (structure: imidazole with 4-OH-phenyl, two 4-(C₂H₅)₂N-phenyl groups, NH) | | 32 | 620 | ++ |
| 2 | | (C₂H₅)₂N–C₆H₄– | (structure: with N(CH₃)₂-phenyl, N–CONHC₂H₅, two 4-(C₂H₅)₂N-phenyl groups) | | 25 | 820 | ++ |

As is clear from the results of Table 4, the triarylimidazole derivatives of the formula (I) are equal to or larger than the known triarylimidazole derivatives in the molecular extinction coefficient. But undesirable influences of compounds contained in the living body samples such as serum are not shown in the case of the triarylimidazole derivatives of the present invention in contrast to the known triarylimidazole derivatives.

EXAMPLE 15

Determination of Hydrogen Peroxide (Measuring Solution)

A measuring solution was prepared by dissolving the following ingredients in 50 mM PIPES - sodium hydroxide buffer solution (pH 7.0):

| Compound (7) | 0.5 mM |
|---|---|
| Peroxidase | 4 U/ml |

(Sample)

Samples were prepared by diluting commercially available aqueous hydrogen peroxide with distilled water to give solutions of 0.5, 1.0, 1.5, 2.0 and 4.0 mM.

(Procedure)

To 3 ml of a measuring solution, 20 μl of a sample was added and mixed well, followed by heating at 37° C. for 5 minutes. Then absorbance ($E_S$) at 660 nm was measured.

Further, using deionized water in place of the sample, a blank value ($E_{B1}$) was measured in the same manner as mentioned above.

(Results)

Figure 2:
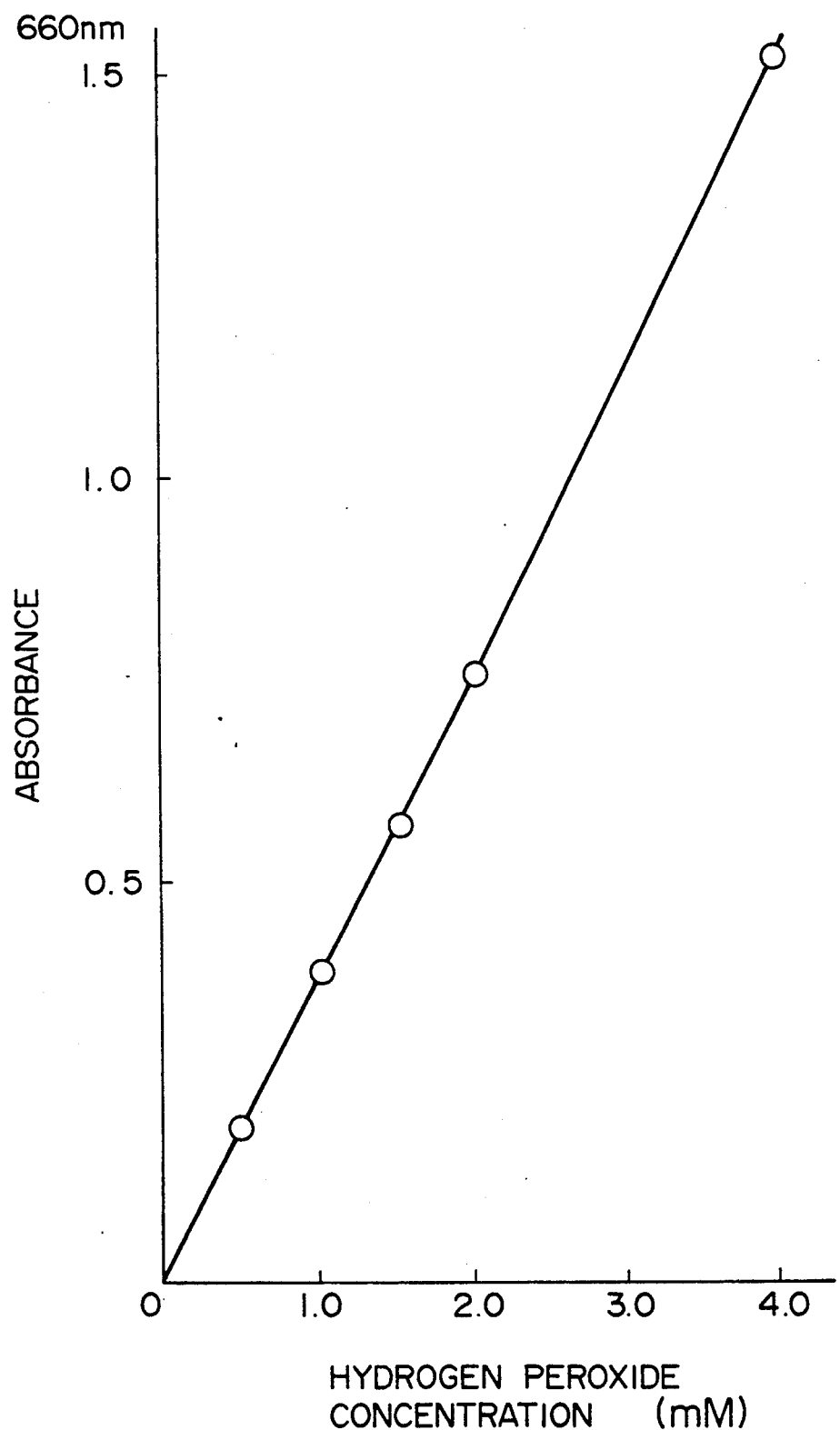
FIG. 2 is a calibration curve obtained in Example 15.

Measured results are shown in FIG. 2.

As is clear from FIG. 2, the calibration curve obtained by lining plotted points as to the absorbance ($E_S - E_{B1}$) taken along the ordinate axis and the hydrogen peroxide concentration taken along the abscissa axis shows good linearity. Therefore, hydrogen peroxide can be determined quantitatively by the process according to the present invention.

The same results were obtained when Compounds (6), (8), (9) and (10) of the present invention were used in place of Compound (7).

EXAMPLE 16

Determination of Hydrogen Peroxide in the Presence of Serum Components (Measuring Solution)

The same as Example 15.

(Sample)

The same as Example 15.

(Procedure)

To 3 ml of a measuring solution, 50 μl of normal human serum or deionized water was added and mixed well. Then, 20 μl of a sample was added to the resulting solution was mixed, followed by heating at 37° C. for 5 minutes. Subsequently, absorbance ($E_S$) at 660 nm was measured.

Using dionized water in place of the sample, a blank value ($E_{B1}$) was measured in the same manner as mentioned above.

(Results)

Measured results are shown in Table 5.

TABLE 5

| $H_2O_2$ concentration in sample (mM) | $E_S - E_{B1}$ In the presence of normal human serum | $E_S - E_{B1}$ In the presence of deionized water |
|---|---|---|
| 0.5 | 0.160 | 0.167 |
| 1.0 | 0.330 | 0.332 |
| 1.5 | 0.482 | 0.490 |
| 2.0 | 0.642 | 0.651 |
| 4.0 | 1.288 | 1.301 |

As is clear from Table 5, when the triarylimidazole derivative of the present invention is used, the dye produced therefrom is hardly influenced by the serum components irrespective of the hydrogen peroxide concentration.

EXAMPLE 17

Determination of Uric Acid (Measuring Solution)

A measuring solution was prepared by dissolving the following reagents in 50 mM PIPES - sodium hydroxide buffer solution (pH 7.0):

| Compound (7) | 0.05 mM |
|---|---|
| Peroxidase | 4 U/ml |
| Uricase | 0.05 U/ml |

(Sample)

Five samples of standard solutions containing 10 mg/dl of uric acid and human serum were prepared.

(Procedure)

To 3 ml of a measuring solution, 20 μl of a sample was added, mixed well, and heated at 37° C. for 5 minutes, followed by measurement of absorbance ($E_S$) at 660 nm.

Further, using deionized water in place of the sample, a blank value ($E_{B1}$) was measured in the same manner as mentioned above.

Concentration of uric acid in human serum was calculated by the following equation:

$$\text{Uric acid (mg/dl)} = \frac{E_S - E_{B1} \text{ of human serum}}{E_S - E_{B1} \text{ of standard solution}} \times 10$$

(Results)

The results are shown in Table 6.

Reference Example 2

Determination of Uric Acid

Using the same samples as used in Example 17 and commercially available kit for measuring uric acid (Uric acid C-Test Wako, a trade name, mfd. by Wako Pure Chemical Industries, ltd.), uric acid concentrations were measured.

The results are also shown in Table 6.

TABLE 6

| Human serum No. | Uric acid values (mg/dl) | |
| --- | --- | --- |
| | Example 17 | Reference Example 1 |
| 1 | 3.2 | 3.3 |
| 2 | 4.2 | 4.3 |
| 3 | 5.3 | 5.3 |
| 4 | 6.9 | 6.9 |
| 5 | 8.8 | 8.9 |

As is clear from Table 6, the measured values of uric acid obtained by the method of Example 17 using the triarylimidazole derivative of the present invention as a color producing component show good correlation with those obtained by using the commercially available kit.

As mentioned above, the triarylimidazole derivatives of the formula (I) are remarkably stable in water or buffer solutions containing surface active agents. Further, the dyes produced from these triarylimidazole derivatives are high in the molecular extinction coefficient, that is, high in the measuring sensitivity. Further, the color production is hardly influenced by components contained in living body samples such as serum according to the present invention.

What is claimed is:

1. A triarylimidazole derivative represented by the formula:

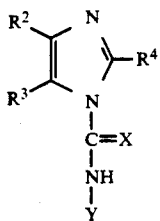

wherein X is an oxygen atom or a sulfur atom; Y is, in the case of X=O, an arylsulfonyl group which may have one or more substituents selected from the group consisting of a lower alkoxy group, a halogen atom and an amino group, an alkylsulfonyl group which may have one or more substituents selected from the group consisting of a lower alkoxy group, a hydroxyl group and a hydroxyethoxy group, a carboxyl group or an alkoxycarbonyl group, or in the case of X=S, a hydrogen atom, an alkyl group which may have one or more substituents selected from the group consisting of a lower alkoxy group, a hydroxyl group, a hydroxyethoxy group and a carboxyl group, an aryl group which may have one or more substituents selected from the group consisting of a lower alkoxy group, a halogen atom, an amino group and a sulfo group, or a hydroxyl group; $R^2$, $R^3$ and $R^4$ are independently an aryl group which may have one or more substituents, provided that at least one of $R^2$, $R^3$ and $R^4$ is a substituted phenyl group having a hydroxyl group or an amino group at the para-position with regard to the imidazole ring, said hydroxyl group or said amino group optionally having one or more substituents.

2. The triarylimidazole derivative according to claim 1, wherein X is an oxygen atom, and Y is an arylsulfonyl group which may have one or more substituents selected from the group consisting of a lower alkoxy group, a halogen atom and an amino group, an alkylsulfonyl group which may have one or more substituents selected from the group consisting of a lower alkoxy group, a hydroxyl group and a hydroxyethoxy group, a carboxyl group or a alkoxycarbonyl group.

3. The triarylimidazole derivative according to claim 1, wherein X is a sulfur atom; and Y is a hydrogen atom, an alkyl group which may have one or more substituents selected from the group consisting of a lower alkoxy group, a hydroxyl group, a hydroxyethoxy group and a carboxyl group, an aryl group which may have one or more substituents selected from the group consisting of a lower alkoxy group, a halogen atom, an amino group and a sulfo group, or a hydroxyl group.

4. A triarylimidazole derivative represented by the formula:

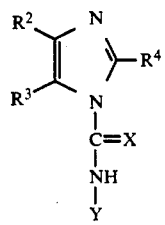

wherein X is an oxygen atom or a sulfur atom; Y is, in the case of X=O, an arylsulfonyl group which may have one or more substituents selected from the group consisting of a lower alkoxy group, a halogen atom and an amino group, wherein the aryl moiety in the arylsulfonyl group is selected from the group consisting of phenyl, tolyl, ethylphenyl, naphthyl and methylnaphthyl, a lower alkylsulfonyl group which may have one ore more substituents selected from the group consisting of a lower alkoxy group, a hydroxyl group and a hydroxyethoxy group, a carboxyl group, or a lower alkoxycarbonyl group, or in the case of X=S, a hydrogen atom, a lower alkyl group which may have one or more substituents selected from the group consisting of a lower alkoxy group, a hydroxyl group, a hydroxyethoxy group and a carboxyl group, an aryl group which is selected from the group consisting of phenyl, tolyl, ethylphenyl, naphthyl and methylnaphthyl which may have one or more substituents selected from the group consisting of a lower alkoxy group, a halogen atom, an amino ground and a sulfo group, or a hydroxyl group; $R^2$, $R^3$ and $R^4$ are independently an aryl group which is selected from the group consisting of phenyl, tolyl, ethylphenyl, naphthyl and methylnaphthyl which may have one or more substituents, provided that at least one of $R^2$, $R^3$ and $R^4$ is a substituted phenyl group having a hydroxyl group or an amino group at the para-position with regard to the imidazole ring, said hydroxyl group or said amino group optionally having one or more substituents.

5. The triarylimidazole derivative according to claim 1, wherein X is an oxygen atom; and Y is an arylsulfonyl group which may have one or more substituents selected from the group consisting of a lower alkoxy group, a halogen atom and an amino group, wherein the aryl moiety in the arylsulfonyl group is selected from the group consisting of phenyl, tolyl, ethylphenyl, naphthyl and methylnaphthyl, a lower alkylsulfonyl group which may have one or more substituents selected from the group consisting of a lower alkoxy group, a hydroxyl group and a hydroxyethoxy group, a carboxyl group or an alkoxycarbonyl group.

6. The triarylimidazole derivative according to claim 1, wherein X is a sulfur atom; and Y is a hydrogen atom, a lower alkyl group which may have one or more substituents selected from the group consisting of a lower alkoxy group, a hydroxyl group, a hydroxyethoxy group and a carboxyl group, an aryl group which is selected from the group consisting of phenyl, tolyl, ethylphenyl, naphthyl and methylnaphthyl which may have one or more substituents selected from the group consisting of a lower alkoxy group, a halogen atom, an amino group and a sulfo group, or a hydroxyl group.

* * * * *